United States Patent [19]

Williams

[11] Patent Number: 4,697,585

[45] Date of Patent: Oct. 6, 1987

[54] APPLIANCE FOR FIXING FRACTURES OF THE FEMUR

[76] Inventor: Michael O. Williams, 1708 E. Canary Ct., Edmond, Okla. 73034

[21] Appl. No.: 690,777

[22] Filed: Jan. 11, 1985

[51] Int. Cl.[4] ............................................. A61F 5/04
[52] U.S. Cl. ........................ 128/92 YZ; 128/92 YY; 128/92 YK
[58] Field of Search ................ 128/92 BC, 92 BB, 83, 128/92 R, 92 YF, 92 YY, 92 YZ, 92 ZW; 603/18, 23

[56] References Cited

U.S. PATENT DOCUMENTS

| | | | |
|---|---|---|---|
| 2,136,471 | 11/1938 | Schneider | 128/92 YZ |
| 2,406,987 | 9/1946 | Anderson | 128/92 ZW |
| 2,675,801 | 4/1954 | Bambara et al. | 128/92 YZ |
| 2,821,979 | 2/1958 | Cameron | 128/92 YY |
| 2,947,308 | 8/1960 | Gorman | 128/92 YF |
| 3,561,437 | 2/1971 | Orlich | 128/92 YX |
| 3,893,196 | 7/1975 | Hochman | 128/92 YZ |
| 4,261,351 | 4/1981 | Scherfel | 128/92 YZ |
| 4,404,693 | 9/1983 | Zweymüller | 623/23 |
| 4,457,301 | 7/1984 | Walker | 128/92 Y |
| 4,475,545 | 10/1984 | Ender | 128/92 YY |

FOREIGN PATENT DOCUMENTS 913228 6/1954 Fed. Rep. of Germany .

OTHER PUBLICATIONS

German Document No. 0118778, Howmedica Internat'l Inc. published Sep. 19, 1984.

German Document No. DE-A-3 244243, Ender, published Jun. 9, 1983.

Primary Examiner—Robert P. Swiatek
Assistant Examiner—J. R. Hakomaki
Attorney, Agent, or Firm—Dunlap, Codding & Peterson

[57] ABSTRACT

An appliance for fixing fractures of the comprises an intramedullary nail for implantation in the intramedullary canal of the femur, a cross nail mountable on the intramedullary nail to extend through the neck of the femur and into the head of the femur and a locking screw that screws into a bore formed in the cross nail to fix the cross nail to the intramedullary nail. A D-shaped aperture is formed through the cross nail to receive the intramedullary nail therethrough and the intramedullary nail has a trifoliate cross section to co-act with the straight side of the aperture to prevent turning of the intramedullary nail in the aperture. A slit is formed longitudinally through the wall of the intramedullary nail and the bore that receives the locking screw is aligned with the slit so that a tapered nose of the locking screw will enter and expand the intramedullary nail into locking engagement with portions of the cross nail extending about the D-shaped aperture. The length of the locking screw is selected to engage the nose thereof with the inside surface of the intramedullary nail and lock the locking screw to the cross nail. Holes are formed through lower portions of the intramedullary nail to receive screws that fix lower portions of the intramedullary nail to lower portions of the femur.

12 Claims, 9 Drawing Figures 4,697,585

APPLIANCE FOR FIXING FRACTURES OF THE FEMUR

BACKGROUND OF THE INVENTION

1. Field of the Invention.

The present invention relates generally to improvements in devices for fixing skeletal fractures and, more particularly, but not by way of limitation, for fixing fractures of the femur.

2. Brief Description of the Prior Art.

In the treatment of fractures of the femur, it has become standard practice to utilize an appliance to fix separated portions of the femur while knitting of such portions occurs. A variety of such appliances are known. For example, U.S. Pat. No. 3,561,437, issued to Orlich, discloses an apparatus which, in one embodiment, is comprised of a plate that can be attached to the lateral side of the femur via screws and a nail that slides in a channel member at the top of the plate for implantation in the head and neck of the femur. In a second embodiment disclosed in the Orlich patent, a nail implanted in the intramedullary canal is used in place of the plate. Another such appliance, disclosed in U.S. Pat. No. 3,439,671, issued to Kuntscher, is comprised of an intramedullary nail that is extended into the intramedullary canal and passes through a hole formed through a femoral spike, or cross nail, that is extended into the head and neck of the femur. Yet another such appliance is that disclosed in U.S. Pat. No. 3,433,220, issued to Zickel, such appliance being comprised of an intramedullary rod that is implanted in the intramedullary canal and has a hole formed through portions thereof near the upper end of the rod to receive a cross nail that is extended into the head and neck of the femur. A locking screw is introduced through the upper end of the intramedullary rod to engage the cross nail and fix the cross nail in position within the hole through the intramedullary rod.

While these prior art appliances have brought about important advances in the treatment of femoral fractures, problems have remained with their use. In general, a particular appliance is limited in the types of fractures for which the appliance is suited. Thus, for example, the Kuntscher appliance is well adapted for the treatment of intertrochanteric fractures but is not well suited for the treatment of comminuted subtrochanteric fractures. In particular, the cross nail of the Kuntscher appliance can shift along the intramedullary nail thereof in response to repeated, small forces that are applied to the cross nail during normal activities of the patient causing shortening of comminuted subtrochanteric fractures of the femur. Similarly, the Zickel appliance is well suited for transverse subtrochanteric fractures of the femur but is not well adapted to fractures that occur in the intertrochanteric, neck and head portions of the femur or comminuted subtrochanteric fractures of the femur. Neither of these two appliances are particularly well adapted to the treatment of fractures of the femoral neck, intertrochanteric region or subtrochanteric region of the femur that occur in association with ipsilateral femoral shaft fractures.

While the problems encountered with the Kuntscher and Zickel appliances can, to some extent, be overcome by using an appliance such as that disclosed by Orlich to include a plate screwed to the lateral surface of the femur, the use of such a plate introduces other problems. In particular, the positioning of the plate on the lateral cortex results in the weight of the body being transmitted to the plate via a lengthy lever arm so that breakage can occur at the upper end of the plate unless upper portions of the plate and connecting portions of the nail are provided with an undesirable bulk. Moreover, the affixation of a plate to the lateral cortex of the femur requires that an incision be made along a considerable extent of the femoral shaft and, in particular, along portions of the femur in which the fracture has occurred. A lengthy incision enhances the likelihood of infection, a problem that can be especially severe when the infection occurs to portions of the bone that have been fractured and whose knitting is the purpose of the use of the appliance.

SUMMARY OF THE INVENTION

The present invention provides an appliance for fixing fractures of the femur that can be used for a wide variety of fractures to include severely comminuted intertrochanteric and subtrochanteric fractures alone or in combination with ipsilateral fractures of the femoral shaft. To this end, the appliance of the present invention is comprised of a tubular intramedullary nail and a cross nail having an aperture formed therethrough to receive the intramedullary nail. The cross nail has a heel portion through which a threaded bore is formed so that a locking screw can be screwed into the heel portion to extend into portions of the cross nail defining the aperture. The intramedullary nail has a slit through the wall thereof that extends longitudinally between the ends of the intramedullary nail and the locking screw is provided with a nose having a tapered portion that permits the nose of the screw to enter the slit formed in the wall of the intramedullary nail and spread the intramedullary nail into tight frictional engagement with portions of the cross nail defining the aperture so that no relative movement can occur between the cross nail and intramedullary nail. The resulting secure locking of the intramedullary nail to the cross nail provides a rigid structure that supports fragments of the femur throughout the shaft, subtrochanteric and intertrochanteric portions thereof to enhance the knitting of such fragments.

An object of the present invention is to provide an appliance for fixing a fractured femur that can be used for a wide variety of types of fractures.

Another object of the present invention is to provide a femoral appliance that is well adapted to the fixation of severely comminuted fractures to the femur occurring throughout the intertrochanteric and subtrochanteric regions.

Yet another object of the invention is to provide a femoral fixation appliance that can be implanted without the need for large incisions into the region of a fracture.

Another object of the invention is to provide a femoral fixation appliance that is both rigid and capable of providing support for fragments of the femur disposed along the length of the femur.

Other objects, features and advantages of the present invention will become clear from the following detailed description of the invention when read in conjunction with the drawings and the appended claims.

DESCRIPTION OF THE PREFERRED EMBODIMENT

Figures 1, 2, 3, 4:
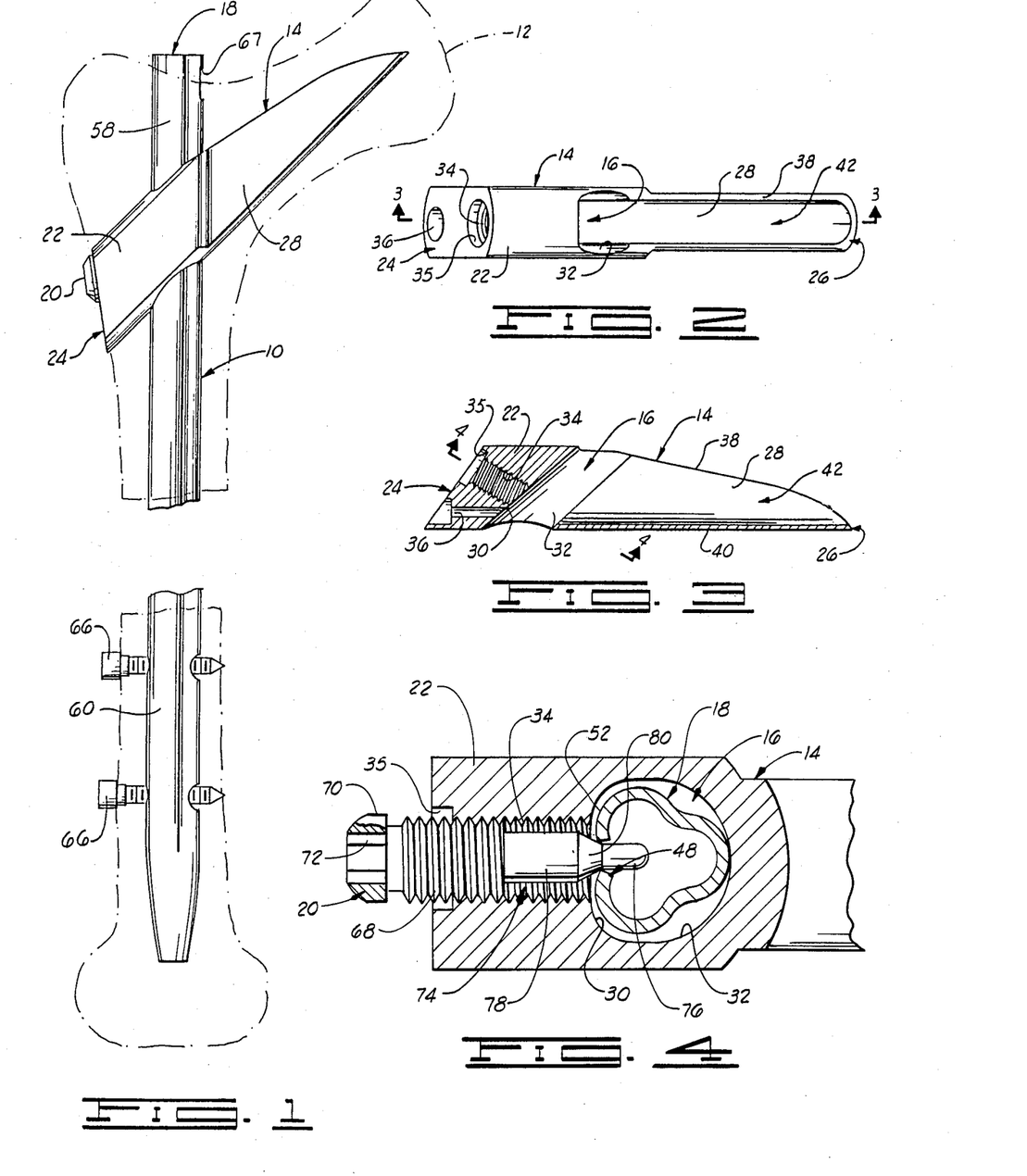
FIG. 1 is a side elevational view of the assembled femoral fixation appliance illustrating the implantation of the appliance in a femur.
FIG. 2 is a plan view of the cross nail of the appliance shown in FIG. 1.
FIG. 3 is a cross section of the cross nail taken along line 3-3 of FIG. 2.
FIG. 4 is a cross section of the cross nail taken along line 4-4 of FIG. 3 and illustrating an unlocked condition of the intramedullary nail.

Referring now to the drawings in general and to FIG. 1 in particular, shown therein and designated by the general reference numeral 10 is an appliance for fixing fractures of the femur constructed in accordance with the present invention. A femur 12 has been drawn in dot-dash line in FIG. 1 to illustrate the position of the appliance 10 after implantation in the femur 12.

The appliance 10 is comprised of a cross nail 14 which, when implanted in the femur 12, extends generally from the base of the greater trochanter and into the head and neck of the femur 12. An aperture 16 (FIGS. 2 and 3) is formed through the cross nail 14 to receive an intramedullary nail 18 that extends downwardly into the intramedullary canal of the femur from a position slightly medial of the tip of the greater trochanter as illustrated in FIG. 1. The appliance 10 is further comprised of a locking screw 20 (FIG. 4) that firmly fixes the intramedullary nail 18 within the aperture 16 of the cross nail 14 in a manner that will be discussed below.

Referring now to FIGS. 2 and 3, shown therein is the construction of the cross nail 14. As illustrated in these Figures, the cross nail 14, which is preferably machined from a bar of type 316L stainless steel, has a heel portion 22 adjacent one end 24 of the cross nail 14. As can be seen in FIG. 1, the end 24 is angled to lie flush with the outer surface of the lateral cortex when the cross nail 14 is implanted in a femur to extend along the axis of the femoral neck. Extending from the heel portion 22 to the opposite end 26 of the cross nail 14, the cross nail 14 is further comprised of a blade portion 28. As can be seen in FIGS. 2 and 3, the aperture 16 is positioned in the blade portion 28 and extends through the cross nail 14 at an angle to the blade portion that is substantially equal to the angle between the neck and shaft of the femur. Thus, the aperture 16 will align the intramedullary nail 18 with the intramedullary canal at such times that the cross nail 14 is implanted in the femur 12 such that the blade portion 28 thereof extends generally parallel to the axis of the neck of the femur as illustrated in FIG. 1.

Figure 5:
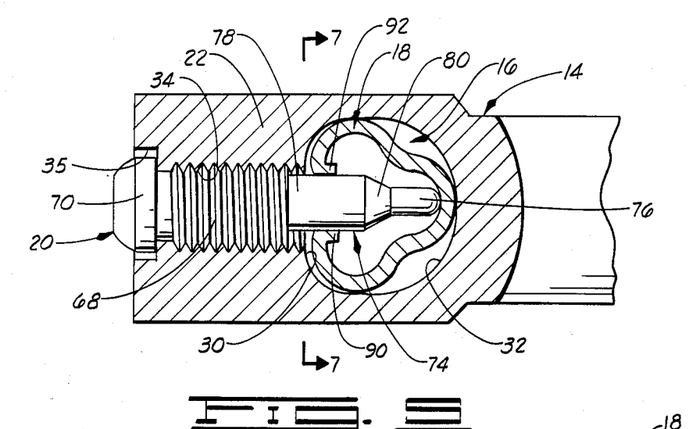
FIG. 5 is a cross section similar to FIG. 4 showing the intramedullary nail in the locked condition thereof.

One aspect of the present invention is the shaping of the aperture 16 through the cross nail 14. In particular, and as shown in FIGS. 4 and 5, the aperture 16 is substantially D-shaped, the aperture 16 being defined by a flattened, internal surface 30 of the heel portion 22, the surface 30 forming the flat side of the D, and a surface 32 of the blade portion 28 that extends arcuately between the ends of the surface 30.

A threaded bore 34 is formed longitudinally through upper portions of the heel portion 22 to intersect the end 24 of the cross nail 14 and the flattened surface 30 of the aperture 16, the axis of the bore 34 extending generally normally to the flattened surface 30 defining the aperture 16. The bore 34 is counterbored from the end 24 of the cross nail 14 to form a socket 35 for a purpose to be discussed below. A hole 36 is formed through the heel portion 22, also intersecting the end 24 of the heel portion 22 of the cross nail 14 and the flattened surface 30 defining the aperture 16, for a purpose also to be discussed below.

The blade portion 28 of the cross nail 14 is rounded at the end 26, as shown in FIG. 2, and has an upper surface 38 that slopes toward the lower side 40 from the heel portion 22 to the end 26 of the cross nail 14. A channel 42 is cut in the upper surface 38 from the end 26 of the cross nail 14 to the aperture 16 so that the blade portion 28 has a generally U-shaped cross section throughout its length. Portions of the blade portion 28 about the surface 32 are broadened to maintain a relatively thick wall for the blade portion 28 throughout the length thereof. Such construction of the cross nail 14 facilitates the implantation of the cross nail 14 in the femur 12 while contributing to a strength and rigidity of the appliance 10 that will permit the appliance 10 to support the weight of the person in which the appliance 10 is implanted.

Figure 8:
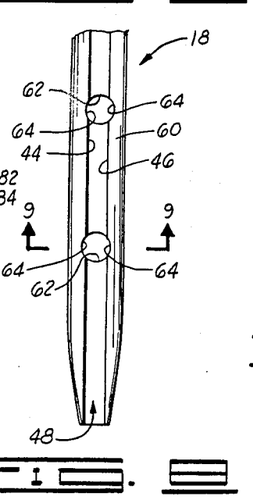
FIG. 8 is a side elevational view of a lower end portion of the intramedullary nail.
Figure 9:
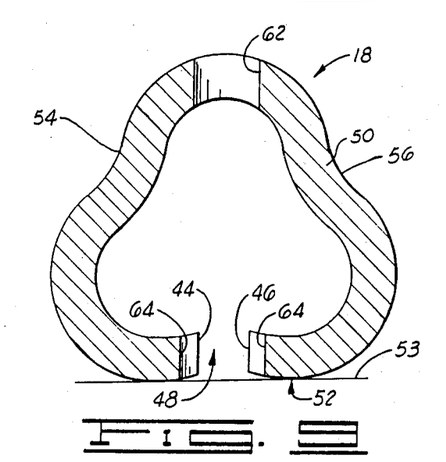
FIG. 9 is a cross section of the intramedullary nail taken along line 9-9 of FIG. 8.

The construction of the intramedullary nail 18 can best be seen from FIGS. 1, 8 and 9. The intramedullary nail 18 is constructed by bending a metal strip, preferably composed of type 316L stainless steel, about the long axis of the strip so that the intramedullary nail 18 has the general form of an elongated tube as indicated in FIG. 1. In the bending of the strip into a tube, a space is left between the side edges 44 and 46 of the strip so that a slit 48 extending the length of the intramedullary nail 18 is formed through the wall 50 of the intramedullary nail 18 at one side 52 thereof. The width of the slit 48 is selected to coact with the locking screw 20 in a manner that will be discussed below. Portions of the wall 50 of the intramedullary nail 18 adjacent the edges 44 and 46 are bent inwardly so that the intramedullary nail 18 has a generally flattened construction, as indicated by the line 53 in FIG. 9, along the side 52 of the intramedullary nail 18. As illustrated in FIG. 4, the flattened side 52 of the intramedullary nail 18 is positioned adjacent the flattened surface 30 formed on the heel portion 22 of the cross nail 14 when the appliance 10 is assembled so that, when the intramedullary nail 18 is inserted through the aperture 16, the side 52 will co-act with the surface 30 to maintain the slit 48 in alignment with the axis of the threaded bore 34 through the heel portion 22 of the cross nail 14.

The flattening of the side 52 is preferably effected by providing the intramedullary nail 18 with a trifoliate cross section and forming the slit 48 between two petals of such cross section. To this end, concavities 54 and 56 are formed in portions of the tubular wall 50 of the intramedullary nail 18 displaced from the slit 48, the concavities 54 and 56 extending substantially the length of the intramedullary nail 18. The trefoliate cross section of the intramedullary nail 18 permits the intramedullary nail 18 to be constructed of a relatively light gauge metal while providing the intramedullary nail 18 with a rigidity sufficient to support the weight of the human body. The present invention contemplates that such rigidity will be exploited in the healing of severely comminuted fractures by using the appliance 10 to maintain the femur in internal traction during the healing of the fracture. In such cases, the femur is placed in traction by the mounting of the cross nail 14 in the upper portions of the femur 12, rigidly securing upper end portions 58 (FIG. 1) of the intramedullary nail 18 to the cross nail 14 in a manner to be discussed below, and by securing lower end portions 60 of the intramedullary nail 18 to lower portions of the femur 12 in a manner shown in FIG. 1. To this end and as shown in FIGS. 8 and 9, one or more holes 62 are formed through the wall 50 in the lower end portion 60 of the intramedullary nail 18, such holes 62 being positioned opposite the side 52 of the intramedullary nail 18 through which the slit 48 is formed. The diameters of the holes 62 are made slightly larger than the width of the slit 48 and arcuate cuts 64 are formed in the edges 44 and 46 defining the slit 48 to align with the holes 62. In particular, the cuts 64 in the edges 44 and 46 are formed on a radius of curvature equal to the radii of the holes 62 to define, with the holes 62, one or more circular passages extending through the intramedullary nail 18 from the side 52 of the intramedullary nail 18 to the opposite side thereof. As shown in FIG. 1, screws 66 can be passed through the passages formed by the holes 62 and cuts 64 to screw into lower portions of the femur 12 when the appliance 10 is implanted in the femur 12. As also shown in FIG. 1, a rectangular hole 67 is formed through the wall of the nail 18 near the upper end thereof to facilitate removal of the appliance 10 from the femur 12 after healing of a fracture has occurred.

Returning now to FIGS. 4 and 5, the locking screw 20 and the manner of locking the intramedullary nail 18 to the cross nail 14 have been illustrated therein. As shown in such Figures, the locking screw 20 has a shank 68 that is provided with external threads to mate with the threads in the bore 34 formed through the heel portion 22 of the cross nail 14 so that the locking screw 20 can be screwed into the hole 34 of the cross nail 14. The locking screw 20 has an enlarged head 70 at one end thereof, the head 70 having a socket 72 formed therein so that the screw 20 can be turned in the bore 34 via a suitable wrench (not shown) having a portion to mate with the socket 72.

As shown in FIG. 5, the head 70 enters the socket 35 of the heel portion 22 when the locking screw 20 is screwed into the bore 34 to precisely position the locking screw 20 in the heel portion 22. The locking screw 20 has a nose 74 at the other end thereof, the nose 74 being constructed in three portions. Immediately adjacent the end of the locking screw opposite the head 70, the nose 74 has a rounded, small diameter portion 76 formed on a diameter substantially equal to the width of the slit 48 so that the small diameter portion 76 will freely enter the slit 48 when the locking screw 20 is screwed into the bore 34 with the intramedullary nail 18 inserted through the aperture 16 of the cross nail 14. Adjacent the shank 68 of the locking screw 20, the nose 74 has a large diameter portion 78 that is formed on a diameter larger than the width of the slit 48. The two portions 76 and 78 of the nose 74 of the locking screw 20 are then connected by a tapered portion 80 that increases steadily in diameter from the diameter of the portion 76 to the diameter of the portion 78.

With the locking screw 20 so constructed, the securing of the cross nail 14 to the intramedullary nail 18 is effected by screwing the locking screw 20 into the bore 34 until the head 70 of the screw 20 seats in socket 35.

In particular, the lengths of the shank 68 and the nose 74 of the locking screw 20 are selected so that, when the head 70 is seated in the socket 35, the large diameter portion of the nose 74 will be extended into the slit 48 in the wall 50 of the intramedullary nail 18 to cause a spreading of the intramedullary nail 18 against portions of the cross nail 14 defining the aperture 16 as illustrated in FIG. 5. Such spreading of the intramedullary nail 18 provides a strong frictional engagement between the intramedullary nail 18 and the cross nail 14 throughout the length of the aperture 16 which will provide a secure connection between the intramedullary nail 18 and the cross nail 14.

The securing of the intramedullary nail 18 to the cross nail 14 in this manner is facilitated by the D-shape of the aperture 16, the flattening of the side 52 of the intramedullary nail 18, and by the selection of the combined length of the shank 68 and nose 74 of the locking screw 20. In particular, and as can be seen in FIG. 4, the flattened construction of the side 52 of the intramedullary nail 18 and the D-shape of the aperture 16, coupled with a selection of the relative sizes of the intramedullary nail 18 and the aperture 16 such that the unexpanded intramedullary nail 18 will fit loosely within the aperture 16, will cause the slit 48 to align with the axis of the bore 34 in the heel portion 22 of the cross nail 14 when the intramedullary nail 18 is inserted through the aperture 16 with the flattened side 52 thereof adjacent the surface 30 on the heel portion 22 of the cross nail 14. When the locking screw 20 is then screwed into the bore 34, the small diameter portion of the nose 74 will engage the in-turned portions of the wall 50 of the intramedullary nail 18 adjacent the slit 48 and be cammed into the slit 48 so that the intramedullary nail 18 will be precisely oriented within the aperture 16 to precisely align the slit 48 with the axis of the bore 34. Further turning of the locking screw 20 into the bore 34 will cause the tapered portion 80 of the nose 74 of the locking screw 20 to enter the slit 48 and commence the expanding of the wall 50 of the intramedullary nail 18 against portions of the cross nail 14 defining the aperture 16. Such expansion continues while the enlarged diameter portion 78 of the nose 74 of the locking screw 20 enters the slit 48 to provide a maximum expansion of the wall 50 of the intramedullary nail 18 that firmly engages the wall 50 with portions of the cross nail 14 defining the aperture 16. Screwing of the locking screw 20 into the bore 34 is then continued until the head 70 seats in the socket 35 to rigidly secure the cross nail to the intramedullary nail.

Figure 6:
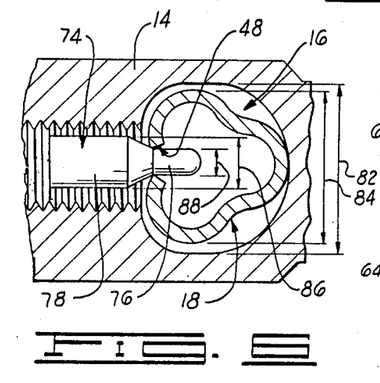
FIG. 6 is a cross section similar to FIG. 4 illustrating dimensional relationships incorporated into the appliance.
Figure 7:
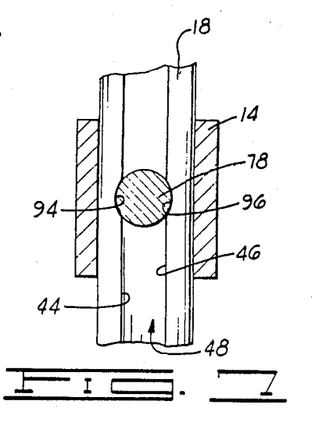
FIG. 7 is a cross section of the cross nail taken along line 7-7 of FIG. 5.

The present invention further contemplates a second mode of locking of the intramedullary nail 18 to the cross nail 14, preventing any sliding movement of the cross nail 14 along the intramedullary nail 18. As shown in FIG. 6, the widths 82 and 84 of the aperture 16 and intramedullary nail 18 are chosen such that the width 82 exceeds the width 84 by a preselected amount when the intramedullary nail 18 is in an unexpanded state. Similarly, the diameter 86 of the enlarged portion 78 of the nose 74 of the locking screw 20 is made larger than the width 88 of the slit 48 by a preselected amount. In the preferred practice of the invention, the preselected amount by which the diameter 86 exceeds the width 88 exceeds the preselected amount by which the width 82 exceeds the width 84. Thus, when the enlarged diameter portion 78 of the nose 74 enters the slit 48, portions of the wall 50 of the intramedullary nail 28 aligned with the bore 34 are crumpled inwardly, as shown at 90 and 92 in FIG. 5, to form arcuate depressions 94 and 96 in the edges 44 and 46 defining the slit 48 about the enlarged portion 78 of the nose 74 of the locking screw 20. These depressions 94 and 96 augment the resistance to sliding of the cross nail 14 on the intramedullary nail 18 that is provided by the frictional engagement of the intramedullary nail 18 with portions of the cross nail 14 defining the aperture 16 that has been discussed above.

The crumpling of the edges 44 and 46 of the intramedullary nail 18 by the enlarged diameter portion 78 of the locking screw nose 74 further serves to fix the locking screw 20 to the intramedullary nail 18 preventing dislodgement of the locking screw 20. Specifically, the crumpled portions 90 and 92 of the intramedullary nail 18 extend a distance along the enlarged diameter portion 78 of the locking screw nose 74 and are forced tightly against the portion 78 by the expansion of the intramedullary nail 18 against portions of the cross nail 14 defining the aperture 16 to form a frictional lock against dislodgement of the locking screw 20 from the intramedullary nail 18.

The locking screw 20 is further locked securely to the cross nail 14 in a manner shown in FIG. 5. In particular, the combined lengths of the shank 68 and nose 74 are selected to cause the nose 74 to engage portions of the inner surface of the wall 50 of the intramedullary nail 18 opposite the slit 48 when the head 70 is seated and thereby force the threads on the shank 68 into firm engagement with the threads of the bore 34. Thus, once the locking screw 20 has been inserted to its maximum extent in the bore 34, a double lock preventing sliding movement of the cross nail 14 on the intramedullary nail 18 is formed so long as the locking screw 20 is emplaced in the cross nail 14 and a second double lock prevents dislodgement of the locking screw 20 from the cross nail 14.

Implantation of the Appliance

For implantation of the appliance 10, the patient is positioned on a fracture table in a supine position with both legs abducted and with the perineum resting against a radiolucent centerpost on the table. The uninjured lower extemity is then elevated and placed in a stirrup so that good lateral radiographs of the hip can be obtained with an image intensifier. The injured lower extremity is then placed in distal traction either through a boot attached to an extension device or through Kirschner wire in either the tibia or the distal femur. In cases involving a shaft fracture, such fracture can be checked with an image intensifier and a crutch can be used to aid in the reduction of the shaft portion of the fracture. Thereafter, the image intensifier is moved to the hip to enable the physician to observe the position of the hip fracture that the appliance 10 is constructed to fix. Following the positioning of the patient on the fracture table, the entire thigh and hip is prepped with Betadine prep and draped with a large laparotomy sheet.

To commence the implantation of the appliance 10 in a fractured hip, an incision having a length of approximately three centimeters is made over the tip of the greater trochanter to permit opening of the intramedullary canal of the proximal femur with an awl. Such opening is made slightly medially of the tip of the greater trochanter and in line with the central axis of the femoral neck slightly anteriorly and laterally of the obturator fossa and the awl is inserted into the intramedullary canal to a depth of two to five centimeters generally in a direction toward the curved axis of the femur.

The awl is then replaced with a ballpoint guide pin which is extended into the femoral shaft across the site of any shaft fractures which may have occurred. During such positioning of the guide pin, the position of the pin with respect to fracture fragments through the region of the hip is checked using the image intensifier in two planes and the image intensifier is similarly utilized to observe the guide pin as the guide pin is manipulated down the femoral shaft and across the site of shaft fractures which might be present.

Following the insertion of the guide pin, the entry portal to the intramedullary canal that has been formed is enlarged by means of a reamer awl inserted over the guide pin. The reamer awl is then removed and the femoral shaft is reamed with a flexible reamer to a diameter slightly larger than the diameter of the intramedullary nail 18 to be used in the fixation of the fracture. In particular, the femoral canal is reamed to a diameter of approximately one-half millimeter to one millimeter larger than the diameter of the intramedullary nail 18, the upper end of the range being necessary when the patient is young or when the bone is extremely hard. The over-reaming of the intramedullary canal will prevent twisting of the intramedullary nail 18 when the nail 18 is subsequently driven down the femoral shaft.

After the reaming of the femoral canal is completed, and the guide wire is removed from the canal, the image intensifier is repositioned at the hip at a 45° angle to the long axis of the femur. A second incision is then made laterally over the base of the greater trochanter to extend distally for a few centimeters and such incision is carried down to the base of the greater trochanter. An important aspect of the present invention is that the second incision is limited to the region of the base of the greater trochanter to limit the avenue for infection that the incision provides and, in particular, to eliminate an avenue for infection to fragments of the femur disposed distally of the intertrochanteric region.

A guide wire is then inserted into the proximal femur at an angle of approximately 135° to extend substantially along the center of the femoral neck. A first hole is then formed in the femur to a depth approximately equal to the length of the heel portion 22 of the cross nail 14 via a cannulated portal reamer that is placed over the guide wire. Once the first hole has been formed, a portal guide or jig (not shown), having two vertically spaced holes is mounted on the guide wire, via the lower hole of the portal guide, and a protruding portion of the portal guide is driven into the first hole laterally in the femur. The portal guide is then fixed to the femur with a secondary Kirschner wire. The second hole is then formed in the femur above the first hole via a portal reamer that is inserted through the upper hole of the portal guide. The two holes through the portal guide are so spaced that the two holes formed in the femur will overlap to form an elliptical hole that will receive the heel portion 22 and widened portions of the blade portion 28 of the cross nail 14 adjacent the heel portion 22 thereof. To this end, the second hole is drilled only to a depth sufficient to receive the heel portion 22 and widened portions of the blade portion 28. The secondary Kirschner wire and the portal guide are then removed from the femur. The formation of the two holes in the positions thus described will permit the cross nail 14 to be driven into the neck and head of the femur in a position that has been indicated in FIG. 1. In particular, the cross nail 14 will extend substantially along the axis of the femoral neck just above the calcar femorale following the implantation of the cross nail in the femur.

Following the removal of the portal guide, the cross nail 14 is placed over the guide wire extending into the femoral neck via the hole 36 formed through the heel portion 22 of the cross nail 14 and the cross nail 14 is driven into the femoral neck. The driving of the cross nail 14 into the femoral neck can be facilitated by a tool (not shown) having a slanted end to mate with the slanted end 24 of the cross nail 14 and having a hole that will align with the threaded bore 34 so that the tool can be connected to the cross nail 14 via a screw (not shown) that screws into the bore 34. As shown in FIG. 3, a portion of the hole 36 that intersects the end 24 of the cross nail 14 is counterbored to receive a projection that can be formed on the driving tool to eliminate any relative motion between the driving tool and the cross nail 14.

Once the cross nail 14 has been driven into the femoral neck and head, the driving tool is removed and replaced with a tool (not shown) that screws to the end 24 of the cross nail 14, via the bore 34, and has a portion that extends upwardly over the aperture 16 formed through the cross nail 14. Such portion has a hole that aligns with the aperture 16 so that a drill can be passed through the hole in such tool and into the aperture 16 to provide a straight path down through the tip of the greater trochanter and the aperture 16 through the cross nail 14.

Following the final alignment of the aperture 16 with the entry hole from the tip of the greater trochanter, the guide tool is removed from the cross nail 14 and a ball tipped guide wire is inserted from the tip of the greater trochanter into the femoral canal and manipulated across fracture sites that may be present in the femur. Such manipulation is observed using the image intensifier and is utilized to position the guide wire such that fragments of the femur will be positioned about the guide wire in substantially the position that such fragments would occupy about the axis of the intramedullary canal in an undamaged femur. The intramedullary nail 18 is then placed over the guide wire with the flattened side 52 thereof directed toward the flattened surface 30 of the heel portion 22 of the cross nail 14 and the intramedullary nail 18 is driven into the intramedullary canal to a depth sufficient to leave approximately one centimeter of the intramedullary nail 18 extending from the top of the femur as indicated in FIG. 1. During the driving of the intramedullary nail 18, it is helpful to tap the cross nail 14 in order to prevent the formation of a sliding lock between the intramedullary nail 18 and the cross nail 14 as the intramedullary nail 18 is driven. Once the intramedullary nail 18 has been driven into the intramedullary canal, the guide wire is removed and the locking screw 20 is screwed into the bore 34 to securely fix the intramedullary nail 18 to the cross nail 14 in the manner described above.

Following the implantation of the appliance 10 in the femur, the lower end portion 60 of the intramedullary nail 18 is secured to lower portions of the femoral shaft. To this end, the image intensifier is repositioned distally to permit the physician to observe the holes 62 through the lower end portion 60 of the intramedullary nail 18. In particular, the image intensifier is positioned such that the image of the cuts 64 align with the image of the holes 62 thereby insuring that the axis of the image intensifier is precisely aligned perpendicularly to the intramedullary nail 18 so that the image intensifier can be used as a guide for drilling holes through the lower portion of the femur in alignment with the passages formed through the lower end portion 60 of the intramedullary nail 18 via the holes 62 and the cuts 64. Following the alignment of the image intensifier, a stab wound is made laterally in the skin and down through the fascialata to receive a drill sleeve that extends to lower portions of the femur. The position of the drill sleeve is checked with lateral and anterior/posterior radiographs obtained with the image intensifier to provide a precise alignment between the drill guide and the passages through the lower end portion 60 of the intramedullary nail 18. Holes are then drilled through the lateral cortex of the femur to pass through the passages in the lower end portion of the intramedullary nail 18 and thence through the medial cortex. The screws 66 are then inserted into the stab wounds through which the holes through the femur were drilled and screwed into the lateral cortex, through the lower end portion 60 of the intramedullary nail 18, and into the medial cortex in a manner that has been shown in FIG. 1. With the screws 66 thus extending both through portions of the femur and lower end portions of the intramedullary nail 18, the appliance 10 will be securely fixed to both the distal and proximal ends of the femur 12 and such fixation will have occurred while the femur is maintained in traction. Thus, in addition to fixing fragments of the femur in the intertrochanteric area, the appliance 10 will also have aligned and positioned fragments of the femur in the subtrochanteric and shaft portions thereof about the intramedullary nail 18 to position all fragments of the femur in substantially the positions such fragments occupy in the uninjured femur to permit the formation of a callus about the fragments to reform the femur into substantially the same configuration that existed prior to the fracture. Following the securing of the lower end portion 60 of the intramedullary nail 18 to the distal portion of the femur, the wounds made in the hip and thigh are closed in the standard fashion.

Aftercare of fractures of the type that are fixed using the appliance 10 consists of allowing the patient to be ambulatory on crutches and allowing at least touch-down of the leg in which the appliance 10 has been implanted. However, full weight bearing on such leg is delayed until substantial healing of the fracture has occurred to prevent the full weight of the body from being borne by the screws 66. By this means, the securing of the appliance 10 to both the distal and proximal ends of the femur will insure that the femur is maintained in traction to consequently insure appropriate knitting of the fragments of the femur. During the period in which the femur heals, physiotherapy involving the full range of motion to the hip and knee is commenced to promote early mobility of the patient. It is recommended that such physiotherapy be commenced as soon post-operatively as the patient can tolerate.

It will be clear that the present invention is well adapted to carry out the objects and attain the ends and advantages mentioned as well as those inherent therein. While a presently preferred embodiment of the invention has been described for purposes of this disclosure, numerous changes may be made which will readily suggest themselves to those skilled in the art and which are encompassed within the spirit of the invention disclosed and as defined in the appended claims.

What is claimed is:

1. An appliance for fixing fractures of the femur, comprising:

a tubular intramedullary nail for implantation in the intramedullary canal of the femur, the intramedullary nail being characterized by an upper end portion in the proximal femur when the appliance is implanted, and a lower end portion positioned in the distal end of the femur when the appliance is implanted, and wherein the intramedullary nail has a longitudinally extending slit formed through the wall thereof along one side of the intramedullary nail;

a cross nail for implantation in the proximal femur, the cross nail having a heel portion at one end thereof and a blade portion extending from the heel portion to the other end of the cross nail for positioning in the head and neck of the femur, wherein an aperture sized to receive the intramedullary nail therethrough is formed through the blade portion of the cross nail at the juncture of said two portions of the cross nail, said aperture extending through the cross nail at an angle to the blade portion substantially equal to the angle between the neck and shaft of the femur, and wherein a threaded bore is formed longitudinally through the heel portion of the cross nail in alignment with the aperture through the blade portion thereof;

a locking screw having a threaded shank for securing the locking screw into said bore and a nose extending from the shank to extend into said aperture in the assembled appliance, wherein said nose has a tapered portion to extend into the slit of the intramedullary nail in the assembled appliance to expand the intramedullary nail into locking engagement with portions of the cross nail extending about said aperture; and means for securing the lower end portion of the intramedullary nail to the distal end of the femur whereby the femoral shaft is maintained in internal traction.

2. The appliance of claim 1 wherein said aperture through the cross nail is characterized as having a D-shaped cross section including a substantially straight side adjacent the heel portion of the cross nail; and wherein the intramedullary nail is characterized as having a flattened construction at the side of the intramedullary nail through which said slit is formed.

3. The appliance of claim 2 wherein the intramedullary nail is further characterized as having a tritoliate cross section and wherein said slit extends longitudinally between two petals of said cross section.

4. The appliance of claim 1 wherein the width of the aperture formed through the cross nail exceeds the width of the unexpanded intramedullary nail by a preselected amount; and wherein the nose of the locking screw comprises a portion, extendable into said slit, havrng a diameter greater than the width of the slit, in the unexpanded condition of the intramedullary nail, by an amount that exceeds said preselected amount that the width of the aperture exceeds the width of the unexpanded intramedullary nail.

5. The appliance of claim 4 wherein the locking screw is further characterized as having an enlarged head at the end of the shank opposite the nose of the locking screw for engaging the heel portion of the cross nail when the locking screw is screwed into said bore; and wherein the shank and nose of the locking screw have a combined length sufficient to engage the nose with the inside surface of the wall of the intramedullary nail, opposite said slit, when the head of the locking screw engages the heel portion of the cross nail.

6. The appliance of claim 4 wherein said aperture through the cross nail is characterized as having a D-shaped cross section including a substantially straight side adjacent the heel portion of the cross nail; and wherein the intramedullary nail is characterized as having a flattened construction at the side of the intramedullary nail through which said slit is formed.

7. The appliance of claim 6 wherein the intramedullary nail is further characterized as having a trefoliate cross section and wherein said slit extends longitudinally between two petals of said cross section.

8. The appliance of claim 1 wherein the locking screw is further characterized as having an enlarged head at the end of the shank opposite the nose of the locking screw for engaging the heel portion of the cross nail when the locking screw is screwed into said bore; and wherein the shank and nose of the locking screw have a combined length sufficient to engage the nose with the inside surface of the wall of the intramedullary nail, opposite said slit, when the head of the locking screw engages the heel portion of the cross nail.

9. An appliance for fixing fractures of the femur, comprising:

a tubular intramedullary nail having a trifoliate cross section, wherein a longitudinally extending slit is formed through the wall of the intramedullary nail between two petals of the trefoliate cross section of the intramedullary nail;

a cross nail having a heel portion at one end thereof and a blade portion extending from the heel portion to the other end of the cross nail, wherein a D-shaped aperture is formed through the blade section of the cross nail to receive the intramedullary nail therethrough, the aperture extending through the cross nail at an angle to the blade portion substantially equal to the angle between the neck and shaft of the femur and the straight side of said aperture extending along the juncture of said two portions of the cross nail, and wherein a threaded bore is formed longitudinally through the heel portion of the cross nail in alignment with said D-shaped aperture through the blade portion thereof; and a locking screw having an externally threaded shank for screwing the locking screw into said bore, an enlarged head at one end of the shank for engaging the heel portion of the cross nail when the locking screw is screwed into said bore, and a nose at the opposite end of the shank for entering said aperture, wherein the nose has a tapered portion to extend into the slit of the intramedullary nail in the assembled appliance to expand the intramedullary nail into locking engagement with portions of the cross nail extending about said D-shaped aperture and wherein the shank and nose of the locking screw have a combined length sufficient to engage the nose with the inside surface of the wall of the intramedullary nail when the head of the locking screw engages the heel portion of the cross nail.

10. An appliance for fixing fractures of the femur, comprising:

a tubular intramedullary nail for implantation in the intramedullary canal of the femur, the intramedullary nail being characterized by an upper end portion in the proximal femur when the appliance is implanted, and a lower end portion positioned in the distal end of the femur when the appliance is implanted;

a cross nail for implantation in the proximal femur, the cross nail having a heel portion at one end thereof and a blade portion extending from the heel portion to the other end of the cross nail for positioning in the head and neck of the femur, and wherein an aperture sized to receive the intramedullary nail therethrough is formed through the blade portion of the cross nail at the juncture of said two portions of the cross nail, said aperture extending through the cross nail at an angle to the blade portion substantially equal to the angle between the neck and shaft of the femur;

means for non-movably securing the cross nail to the intramedullary nail; and means for for securing the lower end portion of the intramedullary nail to the distal end of the femur whereby the femoral shaft is maintained in internal traction.

11. The appliance of claim 10, wherein a threaded bore is formed longitudinally through the heel portion of the cross nail in alignment with the aperture through the blade portion thereof; and wherein the means for non-movably securing the cross nail to the intramedullary nail comprises a locking screw having a threaded shank for securing the locking screw into the threaded bore in the heel portion of the cross nail, and a nose extending from the shank to extend into said aperture in the assembled appliance, the nose having a tapered portion to extend into the slit of the intramedullary nail in the assembled appliance to expand the intramedullary nail into locking engagement with the portions of the cross nail extending about said aperture.

12. The appliance of claim 9 wherein the intramedullary nail is characterized as having an upper end portion positioned through the aperture of the cross nail when the appliance is implanted in the femur, and a lower end portion disposed adjacent the distal end of the femur when the appliance is implanted, and wherein the appliance further comprises:

means for securing the lower end portion of the intramedullary nail to the distal end of the femur, whereby the femoral shaft is maintained in internal traction.

* * * * *

UNITED STATES PATENT AND TRADEMARK OFFICE
CERTIFICATE OF CORRECTION

PATENT NO. : 4,697,585
DATED : October 6, 1987
INVENTOR(S) : Michael O. Williams It is certified that error appears in the above-identified patent and that said Letters Patent is hereby corrected as shown below:

Abstract, line 1, immediately preceding "comprises", insert --femur--.

Col. 7, line 55, delete "cn" and insert --on--.

Col. 11, line 48, delete "tritoliate" and insert --trifoliate--.

Col. 11, line 56, delete "havrng" and insert --having--.

Col. 12, line 11, delete "trefoliate" and insert --trifoliate--.

Col. 12, line 30, delete "trefoliate" and insert --trifoliate--.

Signed and Sealed this

Seventh Day of March, 1989

Attest:

DONALD J. QUIGG

Attesting Officer

Commissioner of Patents and Trademarks